United States Patent
van Doorn et al.

(10) Patent No.: US 9,066,705 B1
(45) Date of Patent: Jun. 30, 2015

(54) HYDRATION AND COMPOSITION MEASUREMENT DEVICE AND TECHNIQUE

(75) Inventors: Eric van Doorn, Frederick, MD (US); Pencheng Lv, Newark, DE (US); Arvind Bhat, Germantown, MD (US); Shan Chiang, Ashburn, VA (US)

(73) Assignee: Intelligent Automation, Inc., Rockville, MD (US)

( * ) Notice: Subject to any disclaimer, the term of this patent is extended or adjusted under 35 U.S.C. 154(b) by 401 days.

(21) Appl. No.: 13/412,092

(22) Filed: Mar. 5, 2012

Related U.S. Application Data

(62) Division of application No. 12/455,994, filed on Jun. 10, 2009, now Pat. No. 8,128,561.

(60) Provisional application No. 61/131,570, filed on Jun. 10, 2008.

(51) Int. Cl.
*A61B 5/00* (2006.01)
*A61B 5/05* (2006.01)

(52) U.S. Cl.
CPC ............. *A61B 5/4875* (2013.01); *A61B 5/0507* (2013.01)

(58) Field of Classification Search
CPC .................................. G01N 22/04; A61B 22/04
USPC .......... 600/300, 306, 307, 309, 310; 324/626, 324/640, 642, 643
See application file for complete search history.

(56) References Cited

FOREIGN PATENT DOCUMENTS

JP 56039447 A * 4/1981 ............. G01N 22/04

* cited by examiner

*Primary Examiner* — Sean Dougherty
(74) *Attorney, Agent, or Firm* — Faegre Baker Daniels, LLP

(57) ABSTRACT

A hydration and composition measurement device and technique that in one embodiment includes a microcontroller; a phase lock loop frequency synthesizer controlled by the microcontroller to generate radio frequencies; a cavity for use in resonating at a set of frequencies; a radio frequency power detector for measuring perturbed cavity resonance; and an analyzer. The hydration and composition measurement device may further include a circulator, which receives frequencies from the phase lock loop frequency synthesizer, and an antenna connected to the circulator and cavity. The cavity may be defined by a metallic material or members, and the cavity includes a hole configured to provide access of tissue to be tested to the cavity.

4 Claims, 3 Drawing Sheets

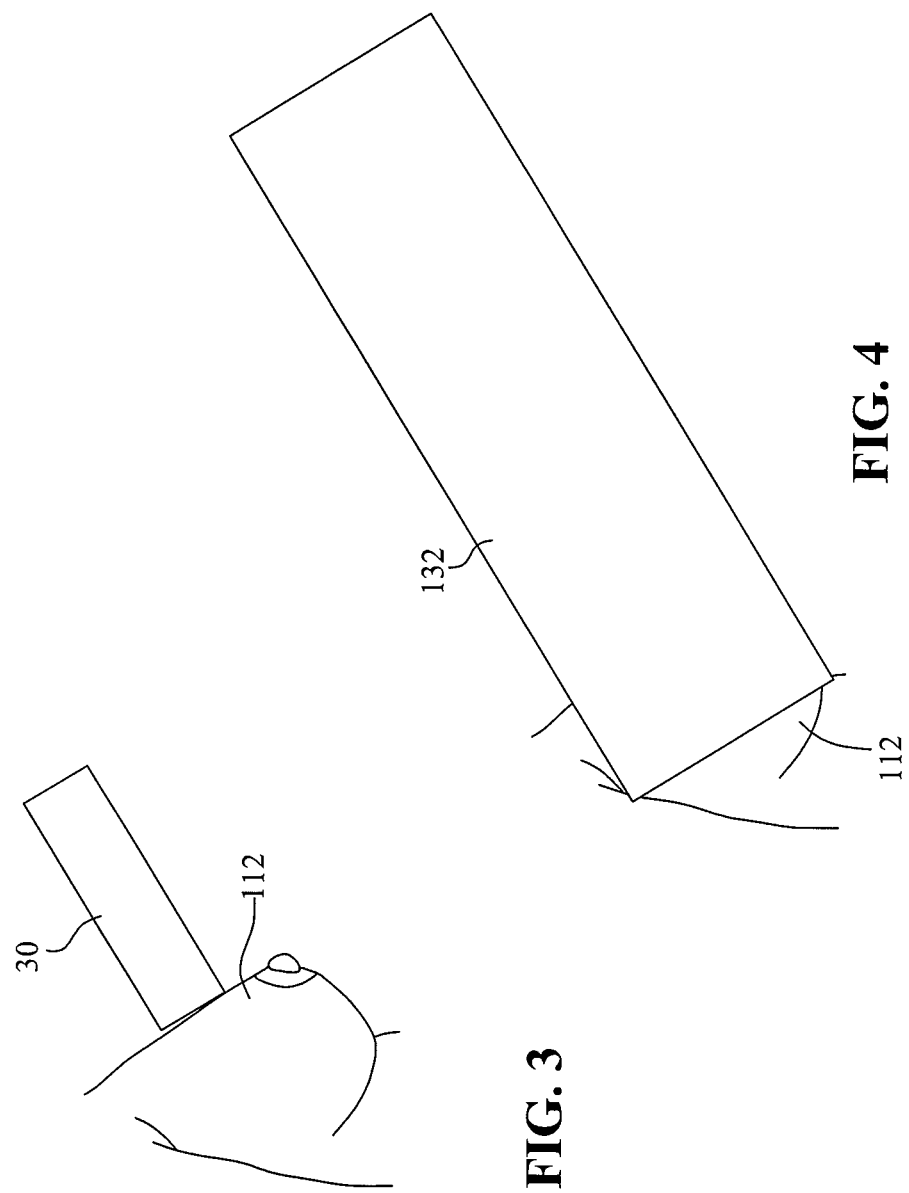

HYDRATION AND COMPOSITION MEASUREMENT DEVICE AND TECHNIQUE

This is a Divisional application claiming priority from Nonprovisional U.S. patent application Ser. No. 12/455,994 filed Jun. 10, 2009, and U.S. Provisional Patent Application Ser. No. 61/131,570 filed Jun. 10, 2008, the entirety of which are incorporated by reference herein.

This invention was made with government support under Contract No. W81XWH-04-C-011 awarded by the U.S. Army. The government has certain rights in the invention.

BACKGROUND OF THE INVENTION

This invention relates to a hydration and composition measurement device and technique, and in particular, to a hydration and composition measuring device that uses a resonant cavity perturbation technique.

Water accounts for approximately 65 percent of the total weight of a normal person, and changes in hydration status can be an indicator for many conditions. For example, diseases, such as hypertension, obesity, renal or kidney failure, and liver failure or cancer, are typically associated with water accumulation/overflooding in the body.

One traditional method of measuring and analyzing a person's hydration status is with deuterated water and Dual Energy X-ray Absorptiometry (DXA). In the deuterated water technique, a patient drinks a known amount of $D_2O$ in a labeled solution. A saliva or urine sample is then collected after an equilibrium period is reached. The sample is then analyzed with a mass spectrometer to determine the dilution factor. The total body water concentration can then be extracted from the dilution factor. DXA hydration status in body composition measurements is considered to be very reliable; however, the prolonged equilibrium time (several hours) and costly mass spectrometer equipment prevent the applications of this method in compact and portable applications. This is because high energy ionizing X-ray radiation is required in this technique, and moreover, the DXA equipment is very bulky and expensive.

More recently, it has been known to use Bio-Impedance Analysis (BIA) to measure hydration status and body composition. This technique involves attaching electrodes to and passing small current through the body. The body impedance can be measured, and the total body water concentration and body composition can be estimated from the body impedance according to calibrated curves. The device used for a BIA technique is much more compact, portable and less expensive than the DXA technique; however, the technique is limited due to its invasive nature and the irreproducibility of the contact resistance of the electrodes.

Another type of testing and measuring technique is called resonant cavity perturbation technique, and it is used to measure a material's dielectric properties in the radio frequency (RF) and microwave frequency regions. With this technique, the material's dielectric properties can be accurately measured with cavity resonance characteristics, including resonance frequency, quality factor and resonance peak intensity. However, heretofore, the resonant cavity perturbation technique required placing the item or person to be tested completely within a cavity or container. In addition, a network analyzer is typically used in the cavity resonance perturbation measurement setup, and the network analyzer is bulky, heavy, and expensive.

Therefore, it is an object of the invention to provide an accurate, efficient personal hydration monitoring device that can be used in identification and treatment of diseases and that is simple for use in both civilian and military sectors.

It is a further object of the invention to provide a hydration and body composition measurement device and technique that utilizes resonant cavity technique and equipment that is compact, relatively low cost, and portable. Also, it would be preferable if conventional off-the-shelf devices can be used to perform the technique.

SUMMARY OF THE INVENTION

In one embodiment of the invention, a hydration and composition measurement device is provided that includes a microcontroller; a phase lock loop frequency synthesizer controlled by the microcontroller to generate radio frequencies; a cavity for use in resonating at a set of frequencies; a radio frequency power detector for measuring perturbed cavity resonance; and an analyzer. The hydration and composition measurement device may further include a circulator, which receives frequencies from the phase lock loop frequency synthesizer, and an antenna connected to the circulator and cavity. The cavity may be defined by a metallic material or members, and the cavity includes a hole configured to provide access of tissue to be tested to the cavity.

The hydration and composition measurement device may also include an analog-to-digital converter, which collects DC voltage from the radio frequency power detector and provides a converted signal to the analyzer, which may be a PC computer. The analog-to-digital converter may also supply a signal back to the microcontroller. Data analyzed by the analyzer can consist of a bell-shaped curve of received radio frequency power vs. frequency.

It is also a feature of the invention to provide a method for measuring hydration and body composition that in one embodiment includes the steps of providing a device capable of measuring a cavity resonance perturbation; resonating a set of frequencies in a cavity of the device; contacting tissue with the cavity to perturb the resonance; measuring the perturbed cavity resonance; analyzing the perturbed cavity resonance; and comparing the value with predetermined values to determine the water content of the tissue.

The cavity can be defined by a metallic material or members and includes a circular hole where the tissue is contacted, and the tissue contacted can be on the biceps or upper leg.

The perturbed cavity resonance can be measured with a radio frequency power detector and converted into a DC voltage. The DC voltage can be collected with an analog-to-digital converter and analyzed with a PC computer. The data analyzed can consist of a bell-shaped curve of received RF power vs. frequency.

The method for measuring hydration and body composition may also include the step of extracting parameters from the bell curve including the width, center of frequency and amplitude. The parameters can follow a monotonic relationship with water content of previously measured tissues having a known water content. The tissue measured can include two parts of an arm such as the bicep and triceps. The use of two or more resonances may be used within the same measurement to correct for varying fat thickness and dielectric properties between different subjects.

It is another feature of the invention to provide a method for measuring hydration and body composition that in one embodiment includes the steps of providing a device capable of measuring a cavity resonance perturbation; resonating a set of frequencies in a cavity of said device; contacting tissue with the cavity to perturb the resonance; measuring the perturbed cavity resonance; analyzing the perturbed cavity resonance; and feeding the measured perturbed cavity resonance to a microcontroller to obtain a steady state operation.

The device for measuring cavity resonance perturbation may include a phase lock loop synthesizer, a circulator, a radio frequency power detector, and an analog-to-digital converter. The device may further include an antenna connected to the circulator and cavity.

BRIEF DESCRIPTION OF THE DRAWINGS

The above-mentioned and other features and objects of this invention and the manner of obtaining them will become more apparent, and the invention itself will be better understood by reference to the following description of embodiments of the present invention taken in conjunction with the accompanying drawing, wherein:

FIG. 3 is a side view of a cavity of a device for measuring personal hydration and body composition being used to measure the hydration of breast tissue; and FIG. 4 is a side view of an alternate embodiment cavity for measuring the hydration and body composition of breast tissue.

Figure 1:
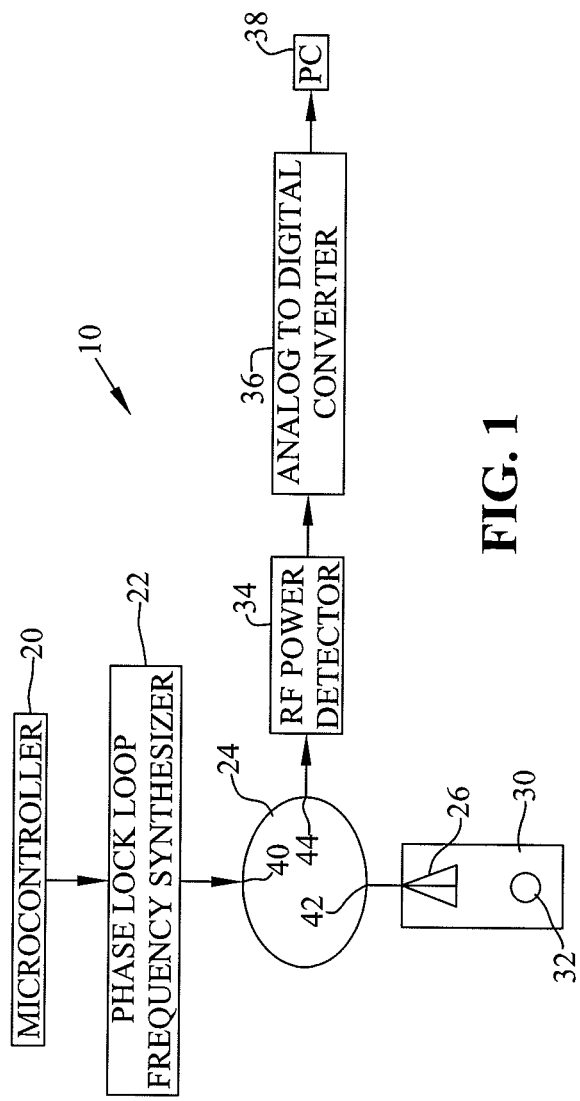
FIG. 1 is a block diagram of a device for measuring personal hydration and body composition.

Corresponding reference characters indicate corresponding parts throughout the several views. Although the drawing represents embodiments of the present invention, the drawing is not necessarily to scale and certain features may be exaggerated in order to better illustrate and explain the present invention. The exemplification set out herein illustrates embodiments of the invention, and such exemplifications are not to be construed as limiting the scope of the invention in any manner.

DETAILED DESCRIPTION OF EMBODIMENTS OF THE INVENTION

For the purpose of promoting an understanding of the principles of the invention, reference will now be made to the embodiments illustrated in the drawing, which are described below. It will nevertheless be understood that no limitation of the scope of the invention is thereby intended. The invention includes any alterations and further modifications in the illustrated devices and described methods and further applications of the principles of the invention, which would normally occur to one skilled in the art to which the invention relates.

The present invention utilizes the resonant cavity perturbation technique, in a compact, reliable, relatively inexpensive, and a virtually non-invasive apparatus is provided to measure the personal hydration and body composition. The present invention may utilize conventional off-the-shelf (COTS) devices.

Now referring to FIG. 1, a diagram of one embodiment of a device for measuring personal hydration and body composition is shown in block form. The hydration and body composition measurement device is shown, generally indicated as 10. Hydration and body composition measurement device 10 includes microcontroller 20, a phase lock loop frequency synthesizer 22, a circulator 24, and an antenna 26. Antenna 26 has a high bandwidth and is connected to and provides feedback from a cavity 30. The cavity may be defined by a metallic material or members, and cavity 30 also includes a circular hole 32 in a bottom plate of the metal cavity. Hydration and body composition measurement device 10 also includes an RF power detector or log detector 34, an analog-to-digital converter 36, and a PC or other device 38 for computing and displaying a hydration and body composition measurement.

The basis of the operation of hydration and body composition measurement device 10 is that the dielectric properties of muscle, fat and other tissues are dramatically different in the RF region and are strongly dependent on water concentrations. Accordingly, measuring the dielectric properties of a tissue allows for the evaluation of the hydration status and body composition.

Phase lock loop frequency synthesizer 22 of hydration and body composition device 10 is controlled by microcontroller 20 to generate RF frequencies. The frequencies are then fed into circulator 24, which is connected to antenna 26. Circulator 24, as is known to one skilled in the art, is a passive electronic component with three or more ports in which the ports are accessed in such a way that when a signal is fed into any port, it is transferred to the next port only. Radio frequencies generated by phase lock loop frequency synthesizer 22 are fed into a first port 40 of circulator 24 and transferred to a second port 42 to which antenna 26 is connected, and the resonant frequency received by antenna 26 is transferred to a third port 44, which is connected to RF power detector 34.

Cavity 30 may be defined by metallic members and is used to resonate a set of frequencies that are determined by the dimensions of cavity 30 and resonance order.

When making a hydration measurement with device 10, the bottom plate of the cavity is pressed to the bare skin at a muscular part of the body (for example, the biceps or upper leg) so that the tissue fills hole 32 of cavity 30. When the tissue is brought into contact with the bottom plate of the cavity 30, the cavity resonance is perturbed. The perturbed cavity resonance is then measured with RF power detector 34, which converts the RF power into a DC voltage. The DC voltage is then collected by analog-to-digital converter 36 and analyzed by the PC and programming loaded thereon.

The data collection process typically takes between 10 to 60 seconds, and the data consists of a bell-shaped curve of received RF power vs. frequency. Parameters are extracted from the curve, specifically, the width (the left and right sides of the bell curve are determined separately), center frequency, and amplitude. The parameters follow a monotonic relationship to the water content of previously measured phantom tissues having a known water content. The results of human subject testing can be used to calculate the sensor response by constructing a table of amplitude, center frequency, and widths vs. hydration.

Figure 2:
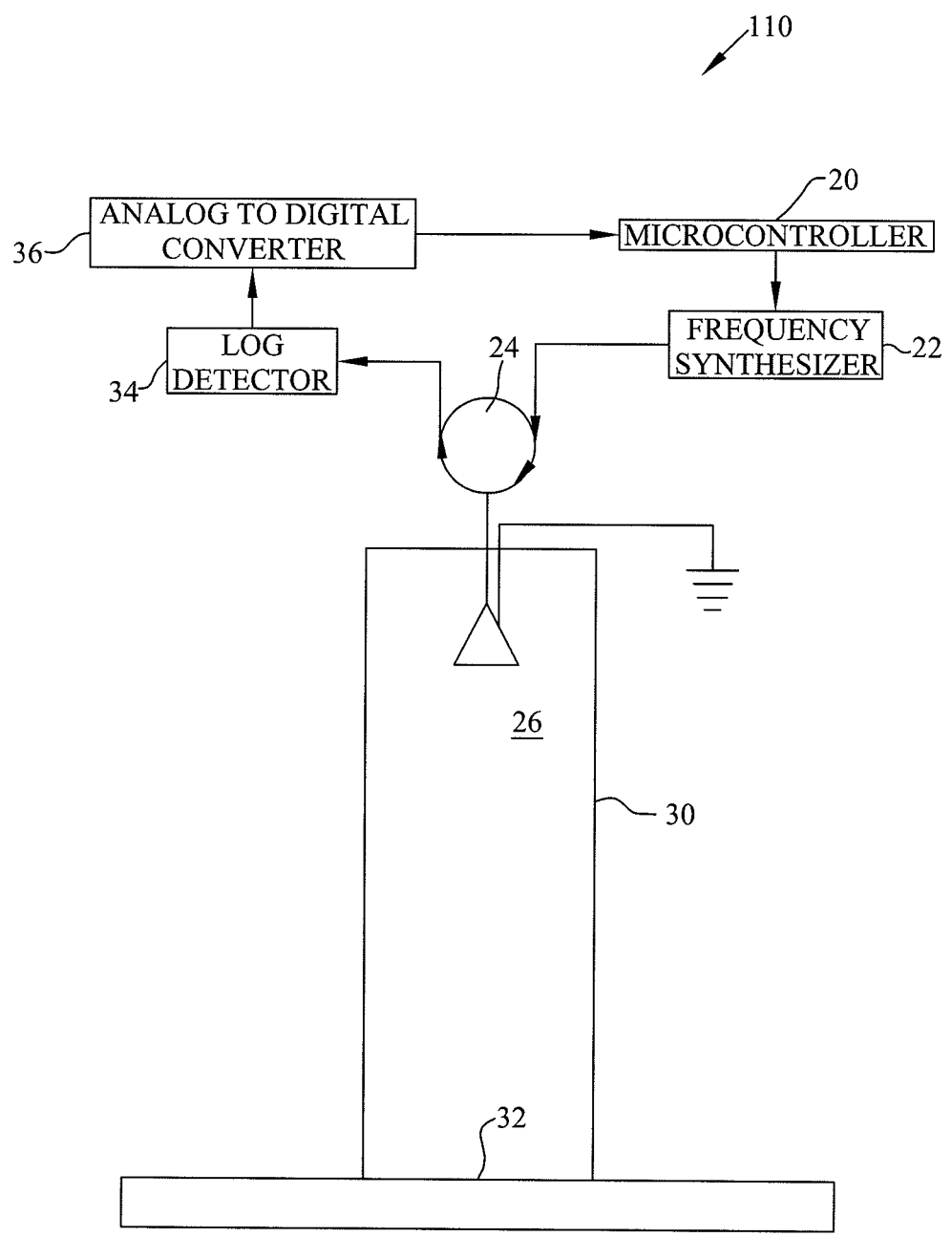
FIG. 2 is a block diagram showing an alternate aspect of a device for measuring personal hydration and body composition.

Now referring to FIG. 2, an alternate embodiment hydration and body composition device is shown, generally indicated as 110. Device 110 is similar to device 10 except that the system provides for a feedback of a measured perturbed cavity resonance from analog-to-digital converter 36 to microcontroller 20. This can be used to obtain a steady state operation. In addition, it should be appreciated that microcontroller 20 may be incorporated into the analytical PC or that two separate units may be utilized.

To decrease or eliminate the effect of fat layer thickness or properties, measurements can be taken on two parts of the arm, one with significant fat, such as the biceps, and one with little fat, such as the triceps. By combining the measurements, a correction can be made based upon the varying fat thickness and dielectric properties between the different subjects. It is also believed that using two or more resonances within the same measurement can enhance the results. A higher frequency will penetrate less far into the body, and be more affected by a fat layer, whereas a lower frequency will penetrate further, and be more affected by a muscle layer. By combining measurements, correction can be made for the varying fat thickness and dielectric properties between different subjects.

One application of the subject invention is to measure the hydration of breast tissue. It is believed that the hydration measurement may be a predictor of the risk of breast cancer. Referring to FIG. 3, one method is shown of placing cavity 30 against breast tissue 112 so that the tissue fills hole 32 of cavity 30. In FIG. 4, an alternate resonant cavity 132 is depicted for testing the hydration of breast tissue 112. Cavity 132 is significantly larger than cavity 130, and the hole therein is large enough for all or a substantial portion of breast tissue 112 to be received therein.

While the invention has been taught with specific reference to these embodiments, one skilled in the art will recognize that changes can be made in form and detail without departing from the spirit and scope of the invention. For example, it should be appreciated that the subject invention may be used to measure or monitor other health conditions. For instance, the device may be used to check for a heart condition associated with the accumulation of water or moisture in the chest. Another potential application is for use in stroke monitoring and detection. The subject invention may be used to monitor jugular vein distention and such distention can be common before a stroke. Furthermore, the subject invention may be used to monitor wounds in the healing process, and in particular, for use for monitoring the healing of pressure wounds or bed sores.

In addition, the subject invention may be used to monitor applications outside of the medical field, such as the detection of mold in a wall. The described embodiments are to be considered, therefore, in all respects only as illustrative and not restrictive. As such, the scope of the invention is indicated by the following claims rather than by the description.

The invention claimed is:

1. A method for measuring hydration and body composition comprising the steps of:
   providing a device capable of measuring a cavity resonance perturbation the device including a phase lock loop frequency synthesizer, a circulator, a radio frequency power detector, and an analog-to-digital converter;
   resonating a set of frequencies in a cavity of said device;
   contacting tissue with the cavity to perturb the resonance;
   measuring the perturbed cavity resonance;
   analyzing the perturbed cavity resonance; and
   feeding the measured perturbed cavity resonance to a microcontroller to obtain a steady state operation, and comparing the perturbed cavity resonance with predetermined values to determine water content of the tissue.

2. The method for measuring hydration and body composition as set forth in claim 1, wherein the device further includes an antenna connected to the circulator and cavity.

3. The method for measuring hydration and body composition as set forth in claim 1, wherein the radio frequency power detector sends a signal to the analog-to-digital converter which in turn sends a signal to the microcontroller.

4. The method for measuring hydration and body composition as set forth in claim 3, wherein the microcontroller sends a signal to the phase lock loop frequency synthesizer as part of obtaining the steady state operation.

* * * * *